(12) United States Patent
Shin

(10) Patent No.: US 6,662,371 B2
(45) Date of Patent: Dec. 16, 2003

(54) RECONFIGURABLE EYEWEAR APPARATUS FOR HEADWEAR VISOR

(76) Inventor: Jae Hoon Shin, Itaewon Dong 258-47, Young San Gu, Seoul (KR)

( * ) Notice: Subject to any disclaimer, the term of this patent is extended or adjusted under 35 U.S.C. 154(b) by 14 days.

(21) Appl. No.: 10/084,223

(22) Filed: Feb. 28, 2002

(65) Prior Publication Data

US 2002/0129433 A1 Sep. 19, 2002

(30) Foreign Application Priority Data

| Mar. 17, 2001 | (KR) | ................................ | 2001-0013953 |
| Mar. 20, 2001 | (KR) | ................................ | 20-2001-0007683 |
| Jun. 21, 2001 | (KR) | ................................ | 2001-0236656 |
| Sep. 26, 2001 | (KR) | ................................ | 10-2001-0059821 |
| Sep. 28, 2001 | (KR) | ................................ | 20-2001-0030086 |

(51) Int. Cl.[7] .................................................. A61F 9/00
(52) U.S. Cl. ............................................................ 2/10
(58) Field of Search ........................... 2/10, 209.13, 422, 2/12, 453; 351/155, 158

(56) References Cited

U.S. PATENT DOCUMENTS

| 1,859,532 A | * | 5/1932 | Rotolo | ............................ | 2/453 |
| 2,004,701 A | * | 6/1935 | Livengood | ........................ | 2/10 |
| 2,549,445 A | * | 4/1951 | Friess | ................................ | 2/10 |
| 2,648,091 A | * | 8/1953 | Jones | ................................ | 2/10 |
| 2,654,089 A | * | 10/1953 | Tannenbaum | ...................... | 2/10 |
| 2,725,560 A | * | 12/1955 | Feldman | .......................... | 2/10 |
| 4,687,420 A | | 8/1987 | Bentley | | |
| 4,819,274 A | | 4/1989 | Day | | |
| 4,869,586 A | * | 9/1989 | Chung | ........................... | 351/158 |
| 5,056,164 A | | 10/1991 | Lisle et al. | | |
| 5,129,102 A | | 7/1992 | Solo | | |
| 5,208,916 A | | 5/1993 | Kelman | | |
| 5,261,124 A | * | 11/1993 | Day | ................................. | 2/10 |
| 5,347,655 A | | 9/1994 | Garrett | | |
| 5,379,491 A | | 1/1995 | Solo | | |
| 5,412,812 A | | 5/1995 | Gatchalian | | |
| 5,422,686 A | | 6/1995 | Kelman et al. | | |
| 5,533,207 A | | 7/1996 | Diaz | | |
| 5,533,208 A | | 7/1996 | Tonoyan et al. | | |
| 5,689,827 A | | 11/1997 | Ryder | | |
| 5,720,040 A | | 2/1998 | Simone | | |
| 5,778,448 A | | 7/1998 | Maher | | |
| 5,819,311 A | | 10/1998 | Lo | | |
| 5,826,271 A | | 10/1998 | Garrett | | |
| 5,966,738 A | | 10/1999 | Wang Lee | | |
| 5,987,640 A | | 11/1999 | Ryder | | |
| 6,173,447 B1 | | 1/2001 | Arnold | | |
| 6,237,156 B1 | | 5/2001 | Ellman et al. | | |
| 6,244,706 B1 | | 6/2001 | Maher | | |

FOREIGN PATENT DOCUMENTS

| KR | 1988-0015000 | 9/1988 |
| KR | 1999-0013748 | 7/1999 |

* cited by examiner

*Primary Examiner*—Rodney M. Lindsey
(74) *Attorney, Agent, or Firm*—Rosenberg, Klein & Lee

(57) ABSTRACT

A reconfigurable eyewear apparatus for a headwear visor is provided. The eyewear apparatus generally includes a support member securable to the headwear visor which defines at least one attachment portion. The apparatus also includes an eyewear assembly adjustably coupled to the support member to be angularly and linearly displaceable between a plurality of eyewear positions relative to the support member. The eyewear apparatus further includes at least one fastening assembly coupled to both the eyewear assembly and support member which serves to releasably lock the eyewear assembly at one of the eyewear positions. The eyewear assembly is formed with a frame having at least one coupling portion, and the fastening assembly is formed with first and second engagement portions. The first and second engagement portions respectively engage in retentive manner the coupling portion of the eyewear assembly frame and the attachment portion of the support member. At least one of the first and second engagement portions is disposed in resiliently biased manner.

20 Claims, 6 Drawing Sheets

RECONFIGURABLE EYEWEAR APPARATUS FOR HEADWEAR VISOR

BACKGROUND OF THE INVENTION

1. Field of the Invention

The subject reconfigurable eyewear apparatus is generally directed to an eyewear apparatus detachably coupled during use to a headwear visor. More specifically, the reconfigurable eyewear apparatus is one whose eyewear assembly suspends downward from the given headwear visor, when in use, to be disposed before the user's eyes, and may be 'flipped,' or angularly displaced, wholly or partially out of the user's direct line of sight when not in use. The subject reconfigurable eyewear apparatus is also one in which such angular reconfiguration of the eyewear assembly is not only conveniently effected, but may also be accompanied by linear displacement from the user's eyes.

It is desirable in many applications to use eyewear of various types coupled to a visor portion that extends longitudinally forward from a particular headwear's cap portion. Numerous examples of such applications abound, as the eyewear's coupling to the visor portion provides greater stability and security of support in maintaining that eyewear positioned before the user's eyes than, for instance, permitting the eyewear to be worn directly on the user's head. Examples of such applications include the attachment of sun-shielding, protective goggle, or corrective lens type eyewear assemblies to the visor, beak, or brim portion of baseball caps, hard hats, and other such types of various headwear.

While ideally quite functional and, therefore, highly desirable in many applications, such visor-attached eyewear are often plagued in practice by a number of functional and structural obstacles. First, the need for ample security of coupling is readily apparent given the delicate structure/configuration of most eyewear and their typical susceptibility to scratching and breakage upon unintentional detachment and droppage from the visor or other supporting portion. Secure coupling is particularly important given the many extreme conditions in which such visor-mounted eyewear often find their use—conditions presented, for instance, by fast-paced and high-impact athletic settings, hazard-rich construction sites, and the like.

Just as essential as the security of coupling, in many cases, though, is the need for quick and convenient reconfigurability or adjustability. The quality of user vision which any given eyewear is invariably intended to preserve demands that the eyewear's lens portion be situated relative to the user's eyes with suitable precision and reliability. Otherwise, the detrimental optical impact may prove prohibitive. A sun-shielding lens portion of a visor-mounted sunglass apparatus positioned too far apart from the user's eyes may, for example, permit the peripheral introduction, or 'leakage,' of sufficient unshielded light to produce excessive glare. This would diminish the clarity of the user's vision and unduly stress his or her optical system. In the case of corrective eyeglass assembly lens portions, the lens portion's improper positioning relative to the user's eyes could well cause a measure of distortion that may noticeably erode the user's visual focus and, again, unduly stress his/her optical system.

These and other equally essential needs, unfortunately, are often found in practice competing one with the other. Where a secure coupling of the eyewear apparatus to the given visor is effectively realized, the rigidity of components, the tightness of their intercoupling, and such other factors tend to impede and limit the free movement of/or between components. On the other hand, a relaxation in the rigidity of components or the tightness of their coupling for the purpose of heightening reconfigurability/adjustability, often diminishes the security of coupling, leaving the eyewear apparatus to be prone to accidental detachment from the visor.

There remains a need, therefore, for a reconfigurable eyewear apparatus that is both securely coupled to a headwear visor and is readily adjustable. There remains a need, moreover, for such reconfigurable eyewear apparatus which may be securely set in various configurations, yet which may be quickly and conveniently adjusted between those configurations.

2. Prior Art

Reconfigurable eyewear devices for headwear visors are known in the art. The best prior art known to Applicant includes U.S. Pat. Nos. #5,129,102; #5,720,040; #6,244,706; #5,778,448; #5,347,655; #5,412,812; #5,056,164; #6,237,156; #6,173,447; #5,987,640; #5,966,738; #5,826,271; #5,819,311; #5,379,491; #5,689,827; #4,687,420; #5,533,207; #5,261,124; #5,533,208; #5,422,686; #5,208,916; #4,869,586; #4,819,274; and, published Korean Patent Applications #20-1999-0013748 and #1988-0015000. Such known devices, however, fail to disclose the unique combination of structural simplicity, stable, secure intercoupling of components, and highly adaptable yet conveniently and reliably actuable adjustability realized by the subject reconfigurable eyewear apparatus.

SUMMARY OF THE INVENTION

It is a primary object of the present invention to provide a reconfigurable eyewear apparatus for a headwear visor which is securely coupled to the visor during use, but which may be quickly and conveniently adjusted in position and orientation.

It is another object of the present invention to provide a reconfigurable eyewear apparatus whose eyewear assembly may be quickly and conveniently displaced angularly and linearly relative to the headwear visor.

It is yet another object of the present invention to provide a reconfigurable eyewear apparatus for a headwear visor that is simple in structure.

These and other objects are attained by a reconfigurable eyewear apparatus for a headwear visor formed in accordance with the present invention. The subject reconfigurable eyewear apparatus generally comprises a support member securable to the headwear visor; an eyewear assembly adjustably coupled to the support member to be angularly and linearly displaceable between a plurality of eyewear positions relative thereto; and, at least one fastening assembly coupled to the eyewear assembly and support member for releasably locking the eyewear assembly at one of the eyewear positions. The support member defines at least one attachment portion, while the eyewear assembly includes a frame having at least one coupling portion. The fastening assembly includes first and second engagement portions respectively engaging in retentive manner the eyewear assembly's frame coupling portion and the support member's attachment portion, with at least one of the first and second engagement portions being disposed in resiliently biased manner.

DETAILED DESCRIPTION OF THE PREFERRED EMBODIMENTS

Figure 1:
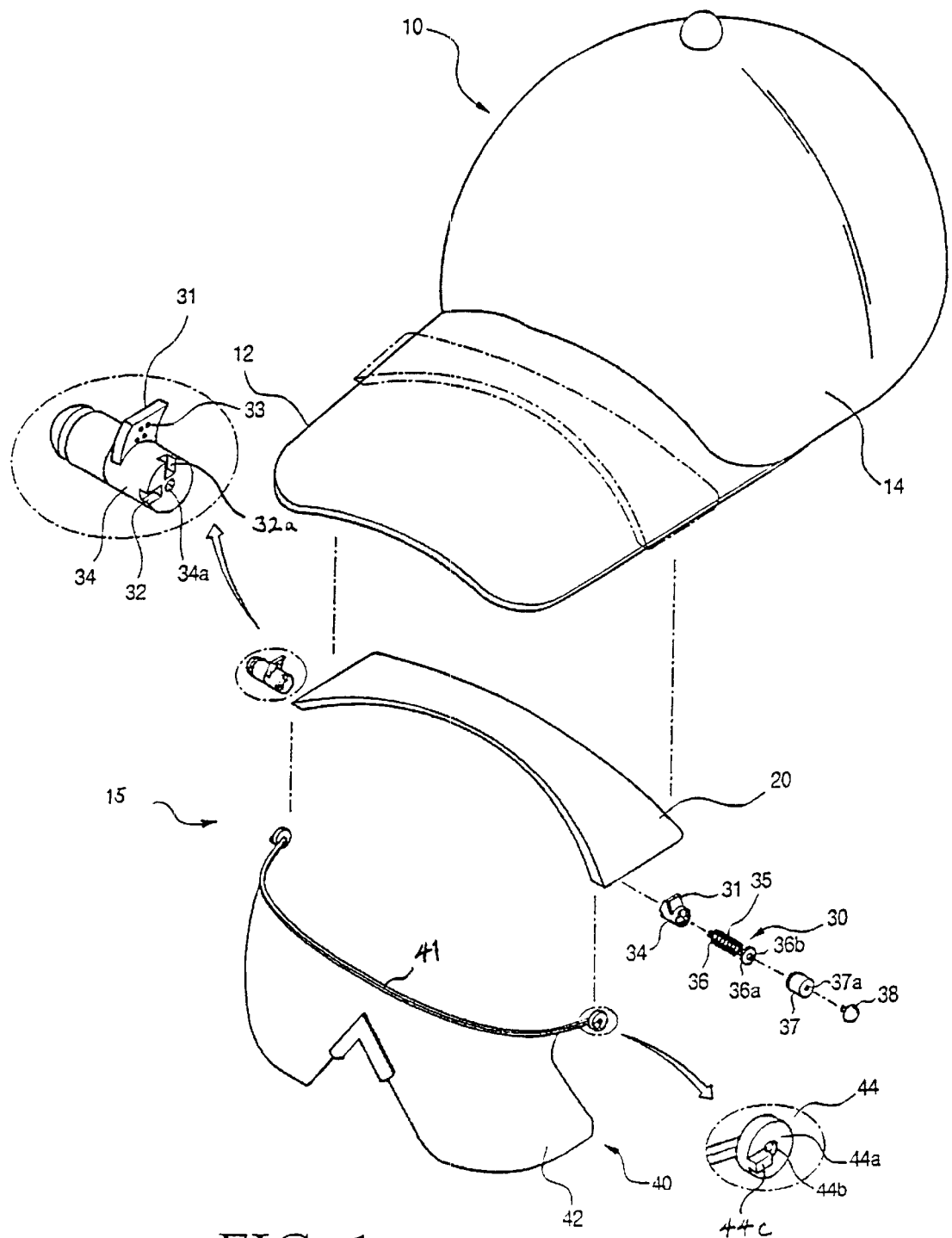
FIG. 1 is an exploded perspective view of a preferred embodiment of the present invention shown applied to a headwear visor.

Referring now to FIG. 1, there is shown one embodiment of the reconfigurable eyewear apparatus formed in accordance with the present invention. The subject eyewear apparatus 15 is shown applied to a visor portion 12 which extends from a cap portion 14 of a headwear device 10. While eyewear apparatus 15 is shown applied to a 'baseball cap' type headwear 10, it may be applied to any other suitable headwear type having a visor, beak, brim, or any other forward projecting portion. Neither the type of headwear nor its particular configuration form any part of the present invention.

Eyewear apparatus 15 generally comprises a support member 20 which may be secured to the visor portion 12 using any suitable measure known in the art; an eyewear assembly 40 adjustably coupled to support member 20; and, at least one fastening assembly 30 coupled to both eyewear assembly 40 and support member 20 for releasably locking eyewear assembly 40 at one of a plurality of eyewear positions relative to support member 20.

Support member 20 is preferably formed as shown with a laterally-extended band configuration suitably dimensioned and contoured to conform to and span at least a substantial lateral width of the visor portion 12. In the embodiment shown, support member 20 is secured to the visor portion 12 for simplicity by passage through a sleeve-like intermediate pocket formed between the visor portion's top and bottom layers. Support member 20 may be formed of a plastic, metallic, or any other suitable material known in the art having a sufficient combination of strength and rigidity to maintain its structural integrity, and thereby support in stable manner the weight of both eyewear assembly 40 and fastening assemblies 30, notwithstanding the conditions presented by the intended application.

Support member 20 extends laterally between a pair of terminal ends. At least one, though preferably both, of the terminal ends is formed with an attachment portion to which a part of at least one fastening assembly 30 adjustably couples. In the embodiment shown, this attachment portion includes a pair of laterally opposed walls which extend from the given terminal end of support member 20 to define a longitudinally extended channel therebetween. One of these walls, preferably the laterally inner-most wall, defines a plurality of receptive parts which may be retentively engaged by one or more corresponding protuberant parts formed on fastening assembly 30. Preferably, such receptive parts are longitudinally offset one from the other to permit selective engagement by the given fastening assembly for its positioning at various points relative to support member 20 (and the user's eyes). Each receptive part preferably defines a through opening having a contour corresponding to that of the fastening assembly's protuberant parts.

In the embodiment shown, support member 20 serves concurrently as a reinforcing rib-structure for the visor portion 12 and as a supporting bracket structure for each fastening assembly 30. Support member 20 may, in alternate embodiments, be formed with any other suitable configuration so long as it provides the necessary receptive part(s) 24 to support each fastening assembly 30 and eyewear assembly 40 with sufficient stability. For example, support member 20 may be formed separately for each lateral side of the visor portion 12 on which a fastening assembly 30 is employed, rather than with the laterally-spanning unitary band structure shown.

Eyewear assembly 40 includes a frame 41 on which a lens portion 42 is coupled. This lens portion may be of any suitable type appropriate for the intended application. In the embodiment shown, for instance, lens portion 42 is tinted and/or polarized to serve a sun shielding/shading function for the resulting sunglass assembly. In other embodiments, such lens portion 42 may be suitably configured to serve vision correcting functions typical of prescription eyeglasses, eye shielding functions typical of protective goggles, and such other functions. The present invention is not limited to any particular choice of configuration for lens portion 42, nor to any particular application in which such lens portion 42 may be employed.

Frame 41 is formed as shown describing a laterally extending contour appropriate for the intended application of eyewear assembly 40. Preferably, frame 41 is formed of a plastic, metallic, or other such material of suitable strength and structural integrity to retain its shape and resist breakage despite repeated and extended use. Depending on the requirements of the intended application and the configuration of the other components, frame 41 may be formed to exhibit more or less, if any, deflection necessary to facilitate secure and stable reconfiguration or adjustment of eyewear assembly 40 without unduly compromising the security of coupling which prevails in apparatus 15.

Frame 41 is equipped at one or more of its lateral ends (depending on the number of fastening assemblies 30 employed in the embodiment) with a coupling portion 44. Each coupling portion 44 includes a body having a substantially planar face 44a into which a threaded bore 44b is centrally formed. Coupling portion 44 is also preferably formed with at least one axial stud 44c extending axially outward from face 44a. Thus configured, each coupling portion 44 serves as a point of releasable retentive engagement for a part of the corresponding fastening assembly 30.

Figure 4:
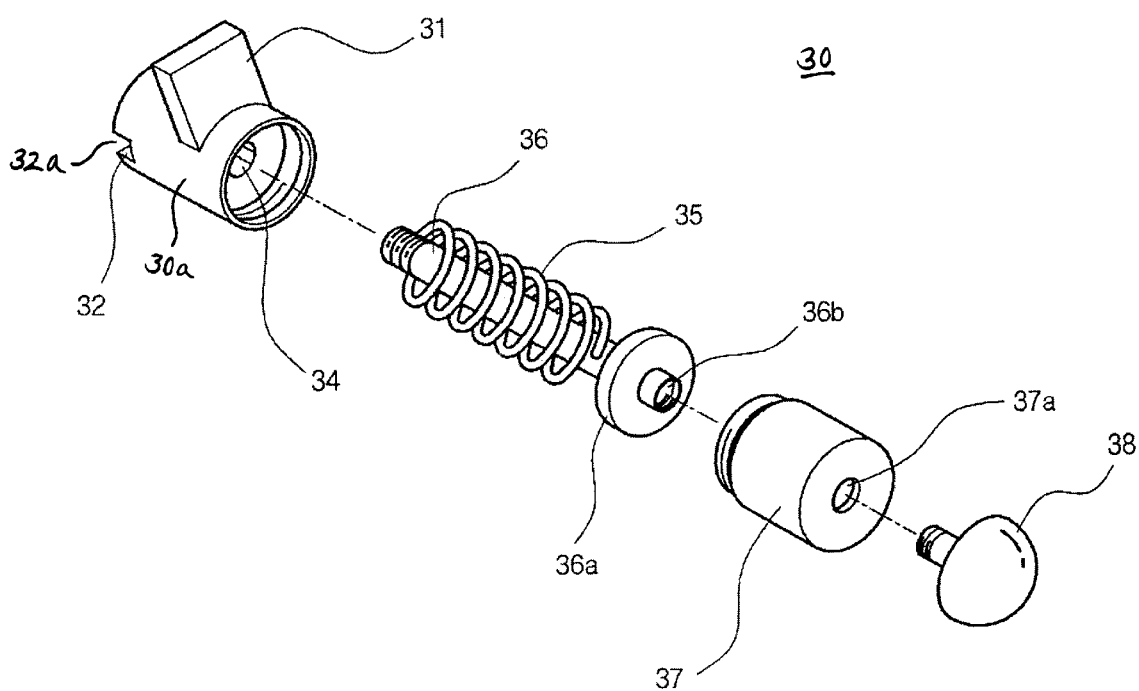
FIG. 4 is an enlarged view of a portion of the perspective view shown in FIG. 1.

Turning next to fastening assembly 30, each fastening assembly 30 serves generally to join eyewear assembly 40 to support member 20 in releasably locked manner. If the requirements of the intended application so permit, the use of one fastening assembly 30 may be sufficient; however, in the embodiment shown, a pair of fastening assemblies 30 are employed at opposing lateral ends of the joined eyewear assembly 40 and support member 20. Each fastening assembly 30 preferably includes, as most clearly shown in FIG. 4, an engagement member 30a having inner and outer axial ends and an intermediate portion extending therebetween. The intermediate portion has formed therein an axially extending through hole 34. Engagement member 30a also includes a first engagement portion 32 defined at its inner axial end, as well as a second engagement portion 31 defined to extend radially from its intermediate portion. Engagement member 30a preferably also includes a threaded section to facilitate the attachment of other fastening assembly components thereto as described in following paragraphs.

The first engagement portion 32 of engagement member 30a includes a substantially planar face in which a plurality of axially extending cavities 32a are formed. Each cavity 32a is suitably contoured and dimensioned to receive stud 44c of a corresponding coupling portion 44 of eyewear assembly frame 41 when the first engagement portion's substantially planar face is brought into engagement with face 44a of that coupling portion 44. Cavities 32a are disposed on the face of first engagement portion 32 to provide selective locking points for the corresponding coupling portion 44. That is, each cavity 32a, when engaged by stud 44c of the given coupling portion 44, that coupling portion 44 (hence, the eyewear assembly 40) is situated at an angular position different from that in which the coupling portion 44 (and eyewear assembly 40) would be situated were that coupling portion's stud 44c to be engaged with a different cavity 32a of the given first engagement portion 32.

In the embodiment shown, a pair of cavities 32a are provided at the first engagement portion 32 of each engagement member 30a. These cavities 30a are offset both in angular position and orientation by approximately 90 degrees to accordingly set the respective 'flipped' and 'in use' positions of eyewear assembly 40. More such cavities 32a may be employed in other embodiments offset in angular position and orientation one from the other by other equal or unequal angular increments, depending on the number of set positions required for eyewear assembly 40.

Figure 2:
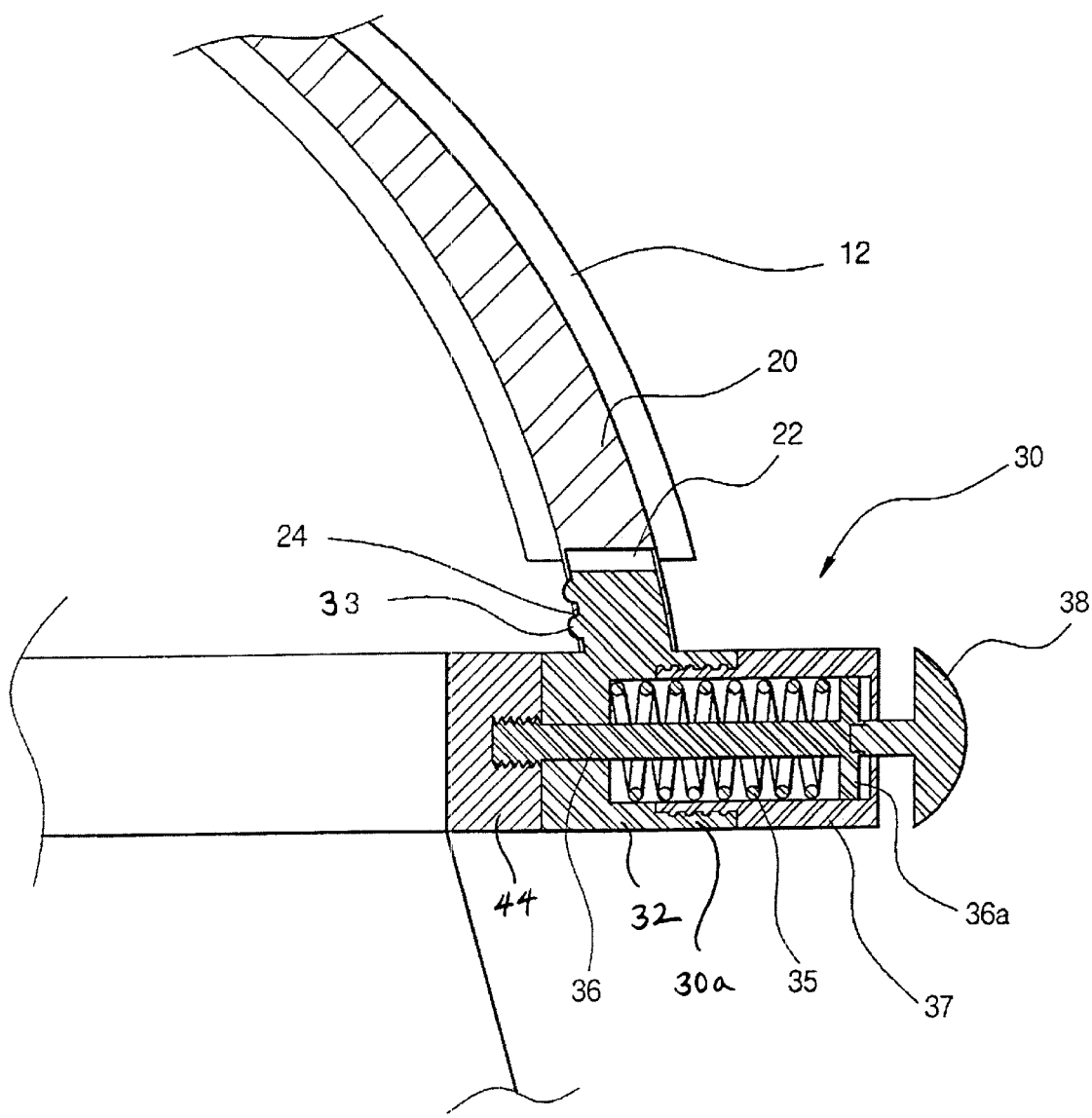
FIG. 2 is a sectional view, partially cutaway, of a portion of the embodiment of the reconfigurable eyewear apparatus shown in FIG. 1, illustrating a locked configuration thereof.
Figure 3:
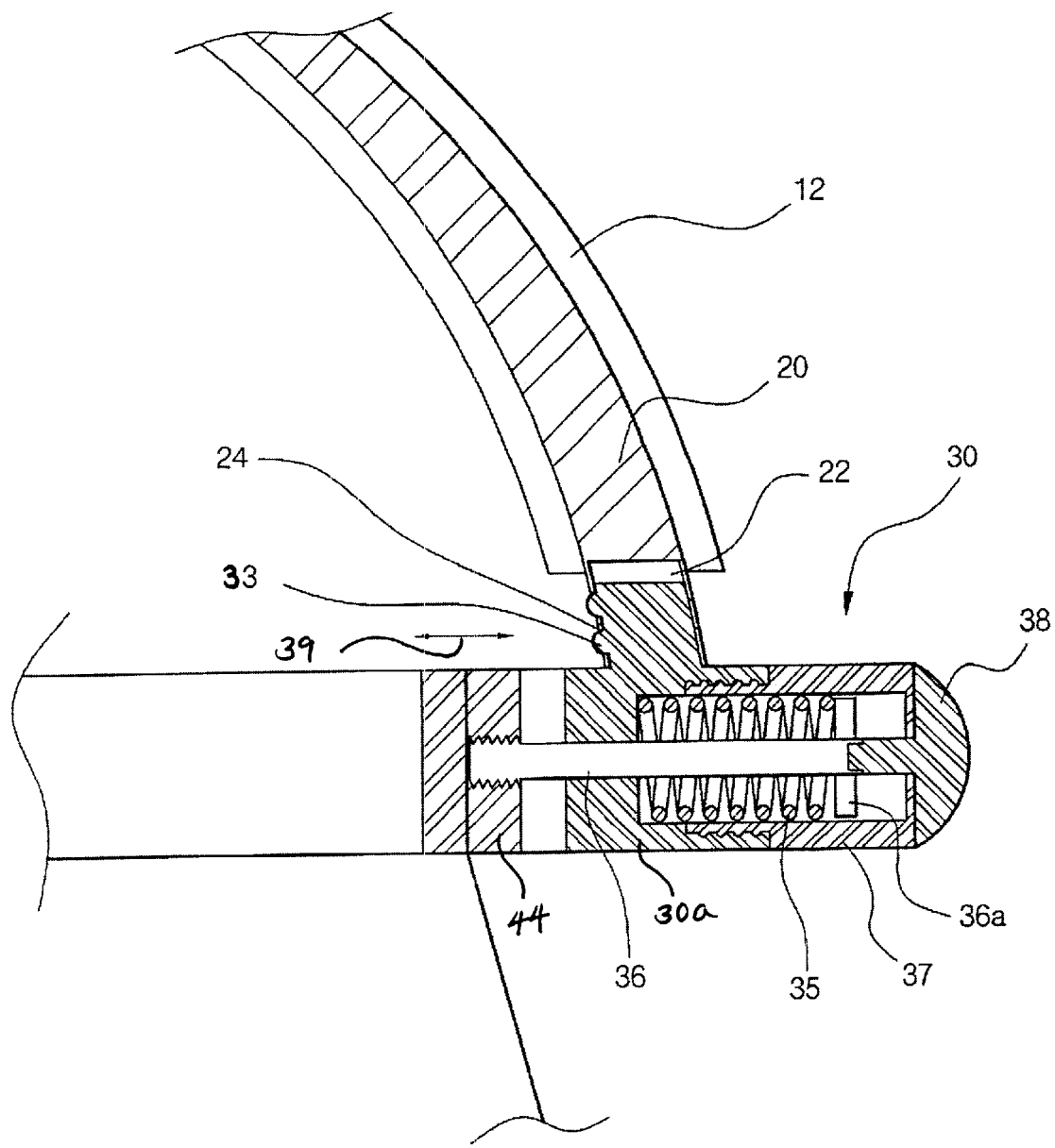
FIG. 3 is a sectional view of the portion shown in FIG. 2, illustrating a released configuration thereof.

Referring back to FIG. 1, and to FIGS. 2–3, the second engagement portion 31 is formed with a substantially rigid block-like configuration. On at least one axially directed face of such second engagement portion 31 is formed at least one protuberant part 33. When apparatus 15 is fully assembled, second engagement portion 31 extends into the longitudinal channel defined by one attachment portion 22 of support member 20. Upon sufficient insert, each protuberant part 33 of second engagement portion 31 engages a through opening of the attachment portion's receptive part 24 to lock engagement member 30a at one of numerous predefined set positions relative to support member 20 (hence, at a set longitudinal displacement from the user's eyes). Preferably, second engagement portion 31 is sufficiently less in longitudinal extent than the longitudinal length of the channel formed by the support member attachment portion 22, such that second engagement portion 31 (and its engagement member 30a) may be widely adjusted in longitudinal position within that channel.

Each second engagement portion 31 is, moreover, preferably formed with more than one protuberant part 33. The set of protuberant parts are accordingly positioned one relative to the other to concurrently engage respective through openings of the given attachment portion's receptive parts 24, and thereby augment the security of coupling. Preferably, each protuberant part 33 is substantially nodular in configuration, such that it facilitates the ease of engagement/disengagement to and from selected ones of such through openings of receptive parts 24.

As mentioned in preceding paragraphs, each attachment portion 22 is preferably formed with a plurality of receptive parts 24 arranged in distributed manner along the longitudinal extent of the channel it defines. Protuberant parts 33 of one second engagement portion 31 may then selectively engage one or more such receptive part through openings to selectively position eyewear assembly 40 at one of numerous set points at different predefined longitudinal spacing from the user's eyes. The adjustability of eyewear assembly 40 between such set points is illustrated by the bidirectional arrow shown in FIG. 5.

Preferably, the block-like body part of each second engagement portion 31 is formed with sufficient lateral thickness to insert snugly into the channel defined by an attachment portion 22. The laterally opposed walls of attachment portion 22 are in this case formed in such manner as to provide at least some degree of deflection to accommodate the second engagement portion's releasable coupling therewith at the numerous set points.

Other configurations of attachment portion 22 and corresponding second engagement portion 31 may be employed in alternate embodiments. For instance, receptive parts 24 may be formed at the laterally outermost wall of attachment portion 22, and protuberant parts 33 may be correspondingly formed at the outwardly directed side of each second engagement portion 31. Alternatively, such receptive parts 24 may be formed at both of the laterally opposed walls of attachment portion 22, and, protuberant parts 33 may be formed at both sides of second engagement portion 31, if the requirements of the intended application so permit. Furthermore, while second engagement portion 31 is configured for insert into the channel defined by attachment portion 22, other embodiments are conceivable where the second engagement portion 31 itself forms an open, channel-defining structure, and attachment portion 22 forms an insert structure received and partially ensleeved thereby.

Referring back to FIG. 4, each fastening assembly 30 preferably includes, further, an axially extended shaft member 36 which passes coaxially through the through hole 34 of engagement member 30a. Shaft member 36 is formed with a threaded inner end portion which emerges from an inner axial opening 34a of the engagement member through hole 34 to threadedly engage bore 44b of an opposing coupling portion 44. Shaft member 36 is formed with a flange member 36a disposed radially thereabout adjacent an outer end portion 36b thereof. Shaft member 36 is preferably of sufficient length that flange member 36a remains offset from the outer axial end of engagement member 30a when fastening assembly 30 is fully assembled.

Disposed about an intermediate portion of shaft member 36 is a resilient member 35, preferably a coil spring element. When fastening assembly 30 is fully assembled, this coil spring element 35 is captured against the outer axial end of engagement member 30a by flange member 36a. Shaft member 36 (and its flange member 36a) is captured within a compartment formed by a cap member 37 that is coupled to the outer axial end of engagement member 30a. Cap member 37 defines a barrel-like configuration having an outer axial wall through which an opening 37a is formed. An actuating member 38 may then be coupled to outer end portion 36b of shaft member 36 through this opening 37a of cap member 37. The resulting assembly permits a user to actuate the release of eyewear assembly 40 from its locked engagement with engagement member 30a and thereafter effect its angular displacement thereof along the direction indicated by the bidirectional arrow 57—by manipulating actuating member 38 to appropriately displace shaft member 36 relative to engagement member 30a.

Referring more closely to FIGS. 2–3, different stages of such actuating displacement effected upon a fastening assembly 30 is illustrated. In FIG. 2, fastening assembly 30 is shown in its normally locked configuration, wherein the first engagement portion 32 of the given fastening assembly 30 is disposed in substantially flush, lockingly engaging contact with the corresponding coupling portion 44 of the eyewear assembly's frame 41. Shaft member 36 at this point is spring biased by the axially outward force resiliently applied by coil spring member 35 against the opposed surfaces of engagement member 30a and flange member 36a. The axially outward bias force thus applied to flange member 36a draws shaft member 36 axially outward to, in turn, draw tightly against engagement member 30a the coupling portion 44 secured to shaft member 36.

When the user wishes to release and angularly adjust, or 'flip,' eyewear assembly 40 between set positions, he or she simply depresses actuating member 38 as shown in FIG. 3. This reversibly displaces coupling portion 44 away from engagement member 30a, as indicated by the bidirectional arrow 39. This then withdraws the coupling portion's stud 44c from the cavity 32 that it had been engaged with, thereby clearing the coupling portion 44 for angular displacement relative to engagement member 30a. The user may then rotate actuating member 38 relative to engagement member 30a, along the direction 57, until stud 44c of coupling portion 44 aligns with another cavity 32a. When the user releases actuating member 38, the compressed coil spring member 35 is released to return to its expanded state, and coupling portion 44 is again drawn into engagement with engagement member 30a, as illustrated in FIG. 2.

Figure 5:
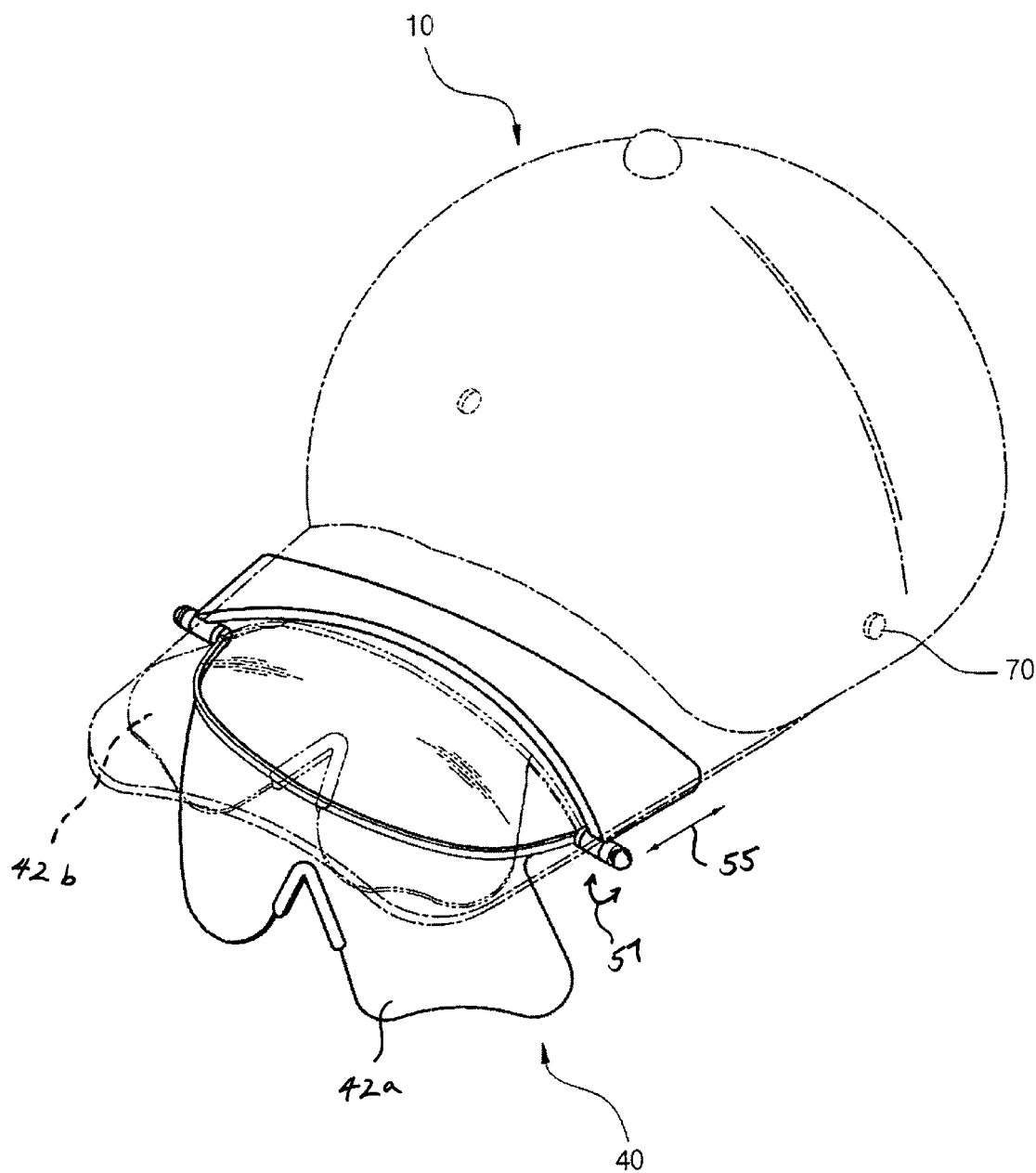
FIG. 5 is an assembled view of the embodiment of the subject reconfigurable eyewear apparatus shown in FIG. 1; and, FIG. 6 is an assembled perspective view of an alternate embodiment of the reconfigurable eyewear apparatus of the present invention shown applied to a headwear visor.

In accordance with the present invention, then, a user may freely and independently adjust both the angular and linear positions of eyewear assembly 40, relative to the headwear 10, and along the directions 57, 55, as shown in FIG. 5. These cavities 32a being offset as shown in the disclosed embodiment—offset by approximately 90 degrees about the central opening 34a of first engagement member 30a, eyewear assembly 40 may be 'flipped' as described in preceding paragraphs between the down, or in use, position 42a and the up, or stowed, position 42b relative to the headwear 10.

As with the corresponding configurations of second engagement portion 31 and coupled support member's attachment portion 22, the corresponding configurations of a first engagement portion 32 and its coupled coupling portion 44 may be varied for other embodiments. For instance, stud 44c may alternately be formed to, instead, extend from engagement member 30a as part of first engagement portion 32. Cavities 32a may accordingly be formed, instead, to extend into coupling portion 44.

The other portions/components of fastening assembly 30 may likewise be varied in configuration in other embodiments. Note, for example, that with other suitable modifications, a resilient member biased normally in a compressed state rather than an expanded state may be employed.

An incidental advantage of the fastening assembly configuration employed in the present embodiment is that the resilient bias force which draws engagement member 30a axially inward against coupling portion 44 of eyewear assembly frame 41 tends also to draw the protuberant parts 33 of second engagement portion 31 into engagement with their respective receptive parts 24 of the support member's attachment portion 22. This reinforcing effect would increase with the rigidity of eyewear assembly 40, particularly with that of the assembly's frame 41.

The present invention is not limited to any particular choice of materials for the various portions/components making up reconfigurable eyewear apparatus 15. Any suitable material known in the art which affords the properties necessary for a given portion/component to serve its intended function, in the manner disclosed herein, may be employed to the extent that the intended application permits. In many applications, of course, the weight of the employed materials will be of significant concern. The choice of materials would accordingly be made to realize an optimum balance of such factor with other factors like strength, durability, toughness, rigidity, and (where appropriate) optical characteristics.

As briefly alluded to in preceding paragraphs, reconfigurable eyewear apparatus 15 may be employed with any of a variety of headwear devices 10. Even for the 'baseball cap' type headwear 10 illustrated in the Figures, various features may be freely employed without effect upon the present invention as herein disclosed. For instance, features such as air holes 70 may be formed on the cap portion of the headwear 10, as illustrated in FIG. 5.

Figure 6:
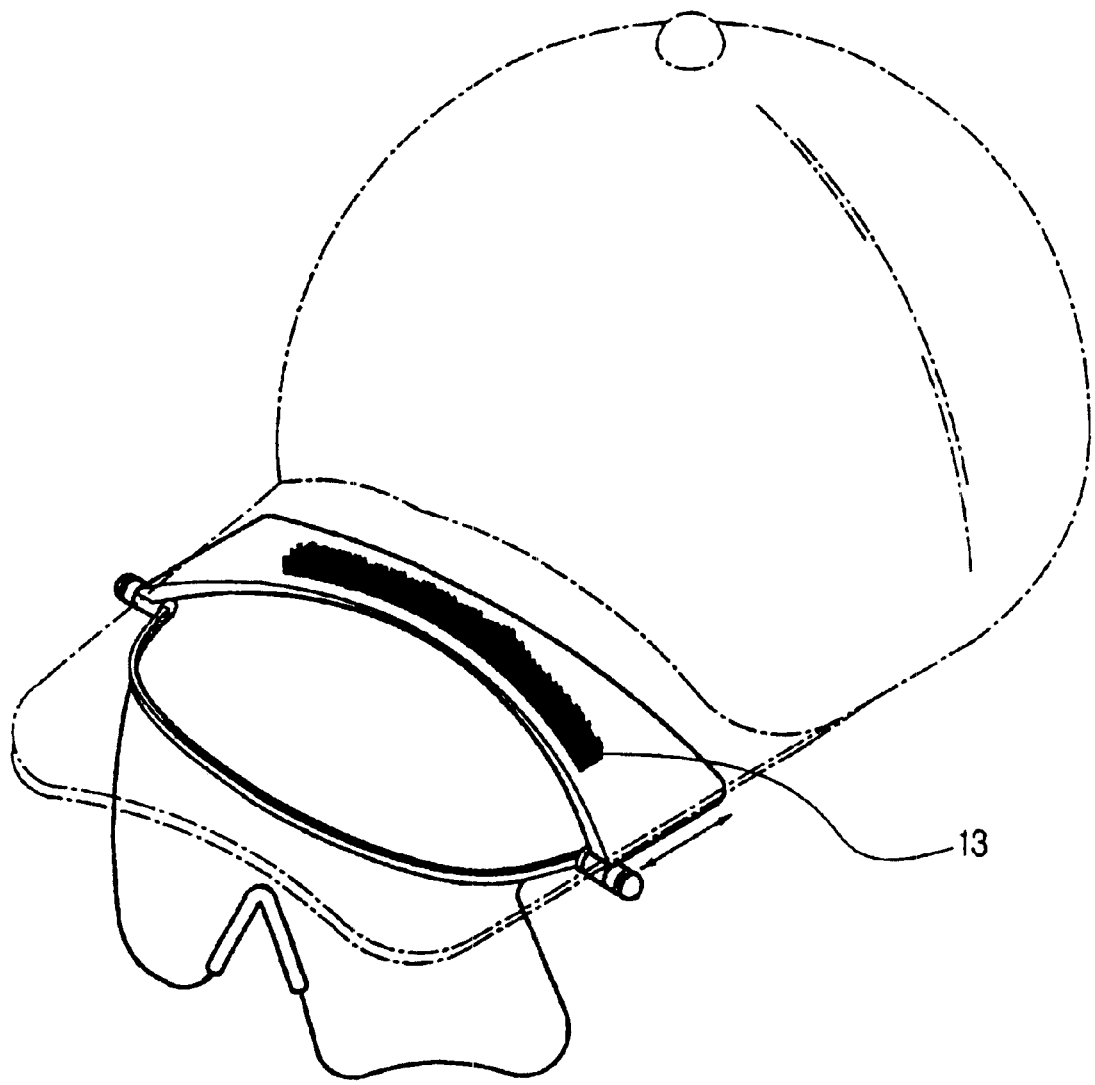

Referring now to FIG. 6, there is shown an alternate embodiment of the present invention wherein support member 20 is simply attached to the bottom surface of the given headwear's visor portion 12, rather than being ensleeved within a pocket formed through that visor portion 12. Any attachment means of sufficient strength may be employed. In the embodiment shown, a hook and loop-type fastening strip 13 is disposed to extend at least partially across the top of support member 20 to detachably engage a complementary hook and loop surface (not shown) either forming or being formed as part of the visor portion's bottom surface. Adhesive or other suitable attachment/fastening means known in the art may be alternatively employed in accordance with the present invention.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, and certain features may be used independently of other features, all without departing from the spirit or scope of the invention as defined in the appended claims.

What is claimed is:

1. A reconfigurable eyewear apparatus for a headwear visor comprising:
   (a) a support member securable to the headwear visor, said support member defining at least one attachment portion;
   (b) an eyewear assembly adjustably coupled to said support member, said eyewear assembly being angularly and linearly displaceable between a plurality of eyewear positions relative to said support member, said eyewear assembly including a frame having at least one coupling portion; and,
   (c) at least one fastening assembly coupled to said eyewear assembly and said support member, said fastening assembly releasably locking said eyewear assembly at one of said eyewear positions, said fastening assembly including first and second engagement portions respectively engaging in retentive manner said eyewear assembly frame coupling portion and said support member attachment portion, at least one of said first and second engagement portions being disposed in resiliently biased manner;
      said first engagement and coupling portions being coaxially disposed along a pivot axis, at least one of said first engagement and coupling portions being axially and pivotally displaceable about said pivot axis for adjustment relative to the other.

2. The reconfigurable eyewear apparatus as recited in claim 1 wherein said frame of said eyewear assembly includes at least a pair of said coupling portions.

3. The reconfigurable eyewear apparatus as recited in claim 2 further comprising at least a pair of said fastening assemblies coupled respectively to said coupling portions of said frame.

4. The reconfigurable eyewear apparatus as recited in claim 1 wherein said fastening assembly includes:

(a) an engagement member having inner and outer axial ends and an intermediate portion extending therebetween, said intermediate portion having an axially extending through hole formed therein, said first engagement portion being defined at said inner axial end, said second engagement portion extending radially from said intermediate portion;

(b) a shaft member having an inner end secured to said coupling portion of said frame and passing through said engagement member through hole; and, (c) a resilient member captured axially between a portion of said shaft member and said engagement member for biasing said shaft member axially outward relative to said engagement member.

5. A reconfigurable eyewear apparatus for a headwear visor comprising:

(a) a support member securable to the headwear visor, said support member defining at least one attachment portion;

(b) an eyewear assembly adjustably coupled to said support member, said eyewear assembly being angularly and linearly displaceable between a plurality of eyewear positions relative to said support member, said eyewear assembly including a frame having at least one coupling portion; and, (c) at least one fastening assembly coupled to said eyewear assembly and said support member, said fastening assembly releasably locking said eyewear assembly at one of said eyewear positions, said fastening assembly including first and second engagement portions respectively engaging in retentive manner said eyewear assembly frame coupling portion and said support member attachment portion, at least one of said first and second engagement portions being disposed in resiliently biased manner;

said fastening assembly further including:
  i. an engagement member having inner and outer axial ends and an intermediate portion extending therebetween, said intermediate portion having an axially extending through hole formed therein, said first engagement portion being defined at said inner axial end, said second engagement portion extending radially from said intermediate portion;
  ii. a shaft member having an inner end secured to said coupling portion of said frame and passing through said engagement member through hole; and,
  iii. a resilient member captured axially between a portion of said shaft member and said engagement member for biasing said shaft member axially outward relative to said engagement member;

one of each mutually engaging pair of said first engagement and coupling portions having a plurality of cavities formed to extend axially therein, and the other of said mutually engaging pair of portions has formed therein at least one axially extending stud for selective insert into one of said cavities, said cavities being angularly offset one from the other.

6. The reconfigurable eyewear apparatus as recited in claim 5 wherein said fastening assembly further includes:

(a) a cap member coupled to said outer axial end of said engagement member to define therebetween a compartment, said resilient member and a portion of said shaft member being disposed therein;

(b) an actuating member coupled to said shaft member, said actuating member having a first portion disposed outside said compartment; and, (c) a flange member fixedly disposed radially about an outer end portion of said shaft member within said compartment for axially capturing said resilient member against said outer axial end of said engagement member.

7. The reconfigurable eyewear apparatus as recited in claim 6 wherein said resilient member includes a coil spring disposed coaxially about a portion of said shaft member.

8. The reconfigurable eyewear apparatus as recited in claim 5 wherein said coupling portion includes one said stud projecting from an axial face thereof, and said first engagement portion has formed therein at least a pair of said cavities angularly offset one from the other by approximately 90 degrees.

9. The reconfigurable eyewear apparatus as recited in claim 4 wherein one of each mutually engaging pair of said second engagement and attachment portions has formed therein a plurality of receptive parts, and the other of said mutually engaging pair of portions has formed thereon at least one protuberant part for selective insert into one of said receptive parts, said receptive parts being longitudinally offset one from the other.

10. The reconfigurable eyewear apparatus as recited in claim 9 wherein each said protuberant part is nodular in configuration, and each said receptive part includes a through opening having a contour corresponding to said protuberant part nodular configuration.

11. A reconfigurable eyewear apparatus for a headwear visor comprising:

(a) a support member securable to the headwear visor, said support member defining at least one attachment portion;

(b) an eyewear assembly adjustably coupled to said support member, said eyewear assembly being angularly and linearly displaceable between a plurality of eyewear positions relative to said support member, said eyewear assembly including a frame having at least one coupling portion; and, (c) at least one fastening assembly coupled to said eyewear assembly and said support member, said fastening assembly releasably locking said eyewear assembly at one of said eyewear positions, said fastening assembly including first and second engagement portions respectively engaging in retentive manner said eyewear assembly frame coupling portion and said support member attachment portion, at least one of said first and second engagement portions being disposed in resiliently biased manner;

said fastening assembly further including:
  i. an engagement member having inner and outer axial ends and an intermediate portion extending therebetween, said intermediate portion having an axially extending through hole formed therein, said first engagement portion being defined at said inner axial end, said second engagement portion extending radially from said intermediate portion;
  ii. a shaft member having an inner end secured to said coupling portion of said frame and passing through said engagement member through hole; and,
  iii. a resilient member captured axially between a portion of said shaft member and said engagement member for biasing said shaft member axially outward relative to said engagement member;

one of each mutually engaging pair of said second engagement and attachment portions having formed therein a plurality of receptive parts, and the other of said mutually engaging pair of portions having formed thereon at least one protuberant part for selective insert into one of said receptive parts, said receptive parts being longitudinally offset one from the other;

wherein said attachment portion includes a pair of laterally opposed walls extending from a terminal end of said support member to define a longitudinally extended channel therebetween, said channel receiving said second engagement portion of said fastening assembly therein, at least one of said walls having said receptive parts formed therein.

12. A reconfigurable eyewear apparatus for a headwear visor comprising:
   (a) a support member securable to the headwear visor, said support member defining at least one attachment portion;
   (b) an eyewear assembly adjustably coupled to said support member, said eyewear assembly being angularly and linearly displaceable between a plurality of eyewear positions relative to said support member, said eyewear assembly including a frame having at least one coupling portion; and,
   (c) at least one fastening assembly coupled to said eyewear assembly and said support member, said fastening assembly releasably locking said eyewear assembly at one of said eyewear positions, said fastening assembly including first and second engagement portions respectively engaging in retentive manner said eyewear assembly frame coupling portion and said support member attachment portion, at least one of said first and second engagement portions being disposed in resiliently biased manner;
   said fastening assembly further including:
      i. an engagement member having inner and outer axial ends and an intermediate portion extending therebetween, said intermediate portion having an axially extending through hole formed therein, said first engagement portion being defined at said inner axial end, said second engagement portion extending radially from said intermediate portion;
      ii. a shaft member having an inner end secured to said coupling portion of said frame and passing through said engagement member through hole; and,
      iii. a resilient member captured axially between a portion of said shaft member and said engagement member for biasing said shaft member axially outward relative to said engagement member;
   one of each mutually engaging pair of said second engagement and attachment portions having formed therein a plurality of receptive parts, and the other of said mutually engaging pair of portions having formed thereon at least one protuberant part for selective insert into one of said receptive parts, said receptive parts being longitudinally offset one from the other;
   wherein said support member includes a laterally extended band configured to conform in contour to the headwear visor, said band having a pair of said attachment portions formed respectively at laterally opposed terminal ends thereof.

13. A reconfigurable eyewear apparatus for a headwear visor comprising:
   (a) a support member securable to the headwear visor, said support member defining at least one attachment portion;
   (b) an eyewear assembly adjustably coupled to said support member, said eyewear assembly being displaceable between a plurality of angular and linear positions relative to said support member, said eyewear assembly including a frame having at least a pair of coupling portions disposed on opposing sides thereof; and,
   (c) at least a pair of fastening assemblies coupled to said eyewear assembly and said support member for concurrently locking said eyewear assembly in releasable manner at one of said angular and one of said linear positions relative to said support assembly, each said fastening assembly including:
      i. an engagement member having a first engagement portion for retentively engaging one said coupling portion of said eyewear assembly frame and a second engagement portion for retentively engaging said attachment portion of said support member, said first engagement and coupling portions being coaxially disposed along a pivot axis, at least one of said first engagement and coupling portions being axially and pivotally displaceable about said pivot axis for adjustment relative to the other; and,
      ii. a shaft member secured to said coupling portion of said eyewear assembly frame and displaceably engaging said engagement member, said shaft member being resiliently biased to a locking position relative to said engagement member, said first and second engagement portions being disposed for retentively engaging respectively said coupling and attachment portions responsive to said shaft member being disposed in said locking position.

14. The reconfigurable eyewear apparatus as recited in claim 13 wherein each said fastening assembly includes a resilient member captured axially between a portion of said shaft member and said engagement member for biasing said shaft member axially outward relative to said engagement member.

15. The reconfigurable eyewear apparatus as recited in claim 14 wherein:
   said engagement member of each said fastening assembly includes inner and outer axial ends and an intermediate portion extending therebetween, said intermediate portion having an axially extending through hole formed therein, said first engagement portion being defined at said inner axial end, said second engagement portion extending radially from said intermediate portion; and,
   said shaft member of each said fastening assembly includes an inner end secured to said coupling portion of said frame and passing through said engagement member through hole.

16. A reconfigurable eyewear apparatus for a headwear visor comprising:
   (a) a support member securable to the headwear visor, said support member defining at least one attachment portion;
   (b) an eyewear assembly adjustably coupled to said support member, said eyewear assembly being displaceable between a plurality of angular and linear positions relative to said support member, said eyewear assembly including a frame having at least a pair of coupling portions disposed on opposing sides thereof; and,
   (c) at least a pair of fastening assemblies coupled to said eyewear assembly and said support member for concurrently locking said eyewear assembly in releasable manner at one of said angular and one of said linear positions relative to said support assembly, each said fastening assembly including:

i. an engagement member having a first engagement portion for retentively engaging one said coupling portion of said eyewear assembly frame and a second engagement portion for retentively engaging said attachment portion of said support member, said engagement member having inner and outer axial ends and an intermediate portion extending therebetween, said intermediate portion having an axially extending through hole formed therein, said first engagement portion being defined at said inner axial end, said second engagement portion extending radially from said intermediate portion;

ii. a shaft member secured to said coupling portion of said eyewear assembly frame and displaceably engaging said engagement member, said shaft member being resiliently biased to a locking position relative to said engagement member, said first and second engagement portions being disposed for retentively engaging respectively said coupling and attachment portions responsive to said shaft member being disposed in said locking position, said shaft member having an inner end secured to one said coupling portion of said frame and passing through said engagement member through hole;

iii. a resilient member captured axially between a portion of said shaft member and said engagement member for biasing said shaft member axially outward relative to said engagement member;

(a) iv. a cap member coupled to said outer axial end of said engagement member to define therebetween a compartment, said resilient member and a portion of said shaft member being disposed therein;

v. an actuating member coupled to said shaft member, said actuating member having a first portion disposed outside said compartment; and, vi. a flange member fixedly disposed radially about an outer end portion of said shaft member within said compartment for axially capturing said resilient member against said outer axial end of said engagement member.

17. A reconfigurable eyewear apparatus for a headwear visor comprising:

(a) a support member securable to the headwear visor, said support member defining at least one attachment portion;

(b) an eyewear assembly adjustably coupled to said support member, said eyewear assembly being displaceable between a plurality of angular and linear positions relative to said support member, said eyewear assembly including a frame having at least a pair of coupling portions disposed on opposing sides thereof; and, (c) at least a pair of fastening assemblies coupled to said eyewear assembly and said support member for concurrently locking said eyewear assembly in releasable manner at one of said angular and one of said linear positions relative to said support assembly, each said fastening assembly including:

i. an engagement member having a first engagement portion for retentively engaging one said coupling portion of said eyewear assembly frame and a second engagement portion for retentively engaging said attachment portion of said support member; and, ii. a shaft member secured to said coupling portion of said eyewear assembly frame and displaceably engaging said engagement member, said shaft member being resiliently biased to a locking position relative to said engagement member, said first and second engagement portions being disposed for retentively engaging respectively said coupling and attachment portions responsive to said shaft member being disposed in said locking position;

wherein one of each mutually engaging pair of said first engagement and coupling portions includes a plurality of cavities formed to extend axially therein, and the other of said mutually engaging pair of portions has formed therein at least one axially extending stud for selective insert into one of said cavities, said cavities being angularly offset one from the other.

18. The reconfigurable eyewear apparatus as recited in claim 13 wherein one of each mutually engaging pair of said second engagement and attachment portions has formed therein a plurality of receptive parts, and the other of said mutually engaging pair of portions has formed thereon at least one protuberant part for selective insert into one of said receptive parts, said receptive parts being longitudinally offset one from the other.

19. A reconfigurable sunglass apparatus for a headwear visor comprising:

(a) a support member securable to the headwear visor, said support member defining a pair of attachment portions each having formed therein a plurality of receptive parts;

(b) a sunglass assembly adjustably coupled to said support member, said eyewear sunglass assembly being pivotally displaceable between at least first and second angular positions relative to said support member and longitudinally displaceable between at least first and second linear positions relative to said support member, said sunglass assembly including a laterally extended frame having at least a pair of coupling portions disposed on opposing sides thereof, each said coupling portion having formed thereon at least one axially extending stud; and, (c) at least a pair of fastening assemblies each coupled to said sunglass assembly and said support member for concurrently locking said sunglass assembly in releasable manner at one of said first and second angular positions and one of said first and second linear positions, each said fastening assembly including:

(1) an engagement member having inner and outer axial ends and an intermediate portion extending therebetween, said intermediate portion having an axially extending through hole formed therein, said inner axial end defining a first engagement portion for retentively engaging one said coupling portion of said sunglass assembly frame, said first engagement portion having a plurality of cavities formed to extend axially therein and disposed angularly offset one from the other for selectively receiving said stud of said coupling portion, said intermediate portion having a second engagement portion extending radially therefrom for retentively engaging one said attachment portion of said support member, said second engagement portion having formed thereon at least one protuberant part for selective insert into one of said receptive parts;

(2) a shaft member secured to said coupling portion of said sunglass assembly frame and slidably engaging said engagement member, said shaft member being resiliently biased to a locking position relative to said engagement member, said first and second engagement portions retentively engaging respectively said coupling and attachment portions responsive to said shaft member being disposed in said locking position; and, (3) a resilient member captured axially between a portion of said shaft member and said engagement member for biasing said shaft member axially outward relative to said engagement member.

20. The reconfigurable eyewear apparatus as recited in claim 19 wherein each said attachment portion includes a pair of laterally opposed walls extending from a terminal end of said support member to define a longitudinally extended channel therebetween, said channel receiving said second engagement portion of said fastening assembly therein, at least one of said walls having said receptive parts formed therein.

* * * * *